United States Patent [19]
Lee-Ruff et al.

[11] Patent Number: 5,580,973
[45] Date of Patent: Dec. 3, 1996

[54] PROCESS FOR PREPARING OPTICALLY ACTIVE NUCLEOSIDES FROM CHIRAL CYCLOBUTANONES

[76] Inventors: Edward Lee-Ruff, 2251 Rodick Road, Unionville, Ontario, Canada, L6C 1R1; Ji-Long Jiang, 4 Assiniboine Road, Suite 1103, North York, Ontario, Canada, M3J 1L2; Wei-Oin Wan, 51 The Chimney Stack Road, Suite 704, North York, Ontario, Canada, M3J 3L9

[21] Appl. No.: 178,566

[22] Filed: Jan. 7, 1994

[51] Int. Cl.$^6$ .................. C07H 1/00; C07H 19/06; C07H 19/16
[52] U.S. Cl. .......... 536/55.3; 536/27.1; 536/28.1
[58] Field of Search ................. 536/18.5, 55.3, 536/18.5, 27.1, 28.1

[56] References Cited

FOREIGN PATENT DOCUMENTS

0458643A2  11/1991  European Pat. Off. .

OTHER PUBLICATIONS

Jung et al. Chemical Abstracts vol. 116, No. 7, Abstr. No. 59875f, Tetrahedron Lett. 32(41):5717–20, 1991.
Borthwick, A. D. et al., Tetrahedron, 48:571, 1992.
Manchand, P. S. et al., J. Org. Chem., 57:3473, 1992.
Beach, J. W. et al., J. Org. Chem., 57:3887, 1992.
Chou, T. S. et al., Synthesis, pp. 565–470, 1992.
Svansson, L. et al., J. Org. Chem., 56:2993, 1991.
Burns, C. L. et al., J. Med. Chem., 36:378, 1993.
Balzarini, J. et al., Biochem. Biophys. Res. Commun., 145:269, 1987.
Morton, D. et al., Adv. in Photochem., 9:197, 1974.
Hayes I. E. E. et al., Can. J. Chem., 67:2057,1989.
Pirrung, M. C. et al., Heterocycles, 25:189, 1987.
Pirrung, M. C. et al., J. Am. Chem. Soc., 111:5824, 1989.
Ahmad, S., Tetrahedron Lett., 32:6997, 1991.
Narasaka, K. et al., Bull. Chem. Soc. Jpn., 64:1471, 1991.
Collington, E. W. et al., J. Chem. Soc. Perkin Trans. 1, pp. 1839, 1990.
Shaw, G., in "Comparative Heterocyclic Chemistry" Katritzky, A. R. and Rees, C. W. (Ed), 5:499, 1984.
Edward L. R. et al., Tetrahedron Letter, 34: 261, 1993.
Tseng, C. K–H, J. Med. Chem. 34:343, 1991.

Primary Examiner—Gary L. Kunz
Attorney, Agent, or Firm—Bereskin & Parr; Philip C. Mendes da Costa

[57] ABSTRACT

A process is disclosed for the preparation of optically active purine nucleosides, particularly nucleosides of formulae 1 and 2, nucleoside analogs and optically active intermediates of formula 3 which may be used in the preparation of nucleosides of the formula 4 as well as a purine nucleosides and nucleoside analogs.

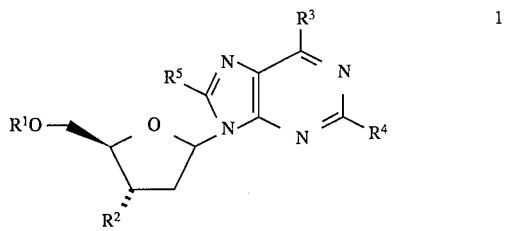

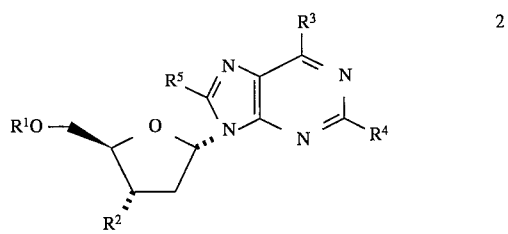

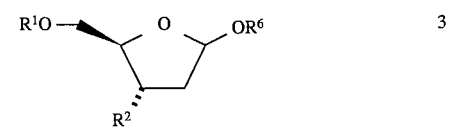

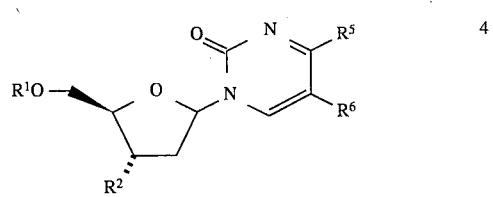

The process is directed to the preparation of such compounds, including novel such compounds in their respective α- and β-anomeric forms, and the enantiomeric forms of these compounds. These compounds show various levels of anti-viral and/or anti-cancer activity.

21 Claims, No Drawings

PROCESS FOR PREPARING OPTICALLY ACTIVE NUCLEOSIDES FROM CHIRAL CYCLOBUTANONES

FIELD OF THE INVENTION

The present invention relates to a process for the preparation of optically active purine nucleosides, particularly nucleosides of formulae 1 and 2, nucleoside analogs and optically active intermediates of formula 3 which may be used in the preparation of nucleosides of the formula 4 as well as a purine nucleosides and nucleoside analogs.

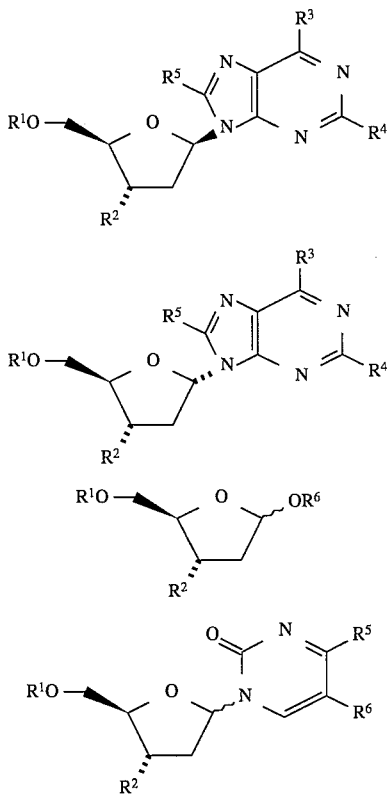

The invention is directed to the preparation of such compounds, including novel such compounds in their respective α- and β-anomeric forms, and the enantiomeric forms of these compounds. These compounds show various levels of anti-viral and/or anti-cancer activity.

BACKGROUND OF THE INVENTION

In recent years, a number of synthetic methods have been described for the preparation of specific carbocyclic (Borthwick, A. D. et al., Tetrahedron, (1992), vol. 48, p. 571) and normal (Manchand, P. S. et al., J. Org. Chem. (1992), vol. 57, p. 3473; Beach J. W. et al., J. Org. Chem. (1992), vol. 57, p. 3887) 2',3'-dideoxynucleosides as potential anti-HIV agents. Many of these syntheses are based on structural modifications of existing nucleosides (Borthwick, A. D. et al., ibid.) or sugar moieties, which are not always conveniently accessible. Other synthetic methods involve the cyclization or annelation of chiral C-3 (Chou, T. S. et al., Synthesis, (1992), p. 565) or C-4 (Svansson, L. et al., J. Org. Chem., (1991), vol. 56, p. 2993) open chain fragments. Many of these synthetic methods involve a sequence of multi-step reactions.

Optically active nucleosides of formulae 1 ($R^3$=OR where R is an alkyl group with unbranched or branched chains spanning 1 to 10 carbons, $R^1$=$R^2$=$R^4$=$R^5$=H) have been reported in Burns, C. L. et al., J. Med. Chem., (1993), vol. 36. p. 378 to show various levels of anti-viral activity. A compound of the formula 1 ($R^1$=$R^2$=$R^5$=H, $R^3$=$R^4$=$NH_2$) has been described as having activity as an HIV inhibitor in Balzarini, J. et al., Biochem. Biophys. Res. Commun., (1987), vol. 145, p. 269. Compounds of the formula 1 and 2 ($R^1$=$R^4$=$R^5$=H, $R^2$=$CH_2OH$, $R^3$=$NH_2$) have been prepared in optically active form as reported in Svansson, L. et al., ibid. Compounds of the formula 4 in the α- and β-forms ($R^1$=H, $R^2$=$CH_2OH$, $R^5$=OH or carbonyl form, $R^6$=$CH_3$) as well as compound 3 ($R^1$=benzoyl, $R^2$=benzoyloxymethyl) have been prepared in optically active form as reported in Svansson, L. et al., ibid.

It is known to photo-excite cyclobutanone to a ring-expanded oxacarbene and to insert this species into OH functions to give cyclic acetals. The general photochemistry has been reviewed, most notably in Morton, D. et al., Adv. in Photochem. (1974), vol. 9, p. 197. It is also known that the oxacarbene inserts into N—H functions (Hayes, I.E.E. et al., Can. J. Chem., (1989), vol. 67, p. 2057; Pirrung, M. C. et al., Heterocycles, (1987), vol. 25, p. 189 and J. Am. Chem. Soc., (1989), vol. 111, p. 5824. The Hayes, I.E.E. et al. paper demonstrate the ability for N—H insertion with respect to a parent purine by an oxacarbene. However, substituent effects on cyclobutanones can have a strong influence on the outcome of these reactions (Morton et al., ibid.)

We have now found that cyclobutanones suitably substituted to prepare nucleosides can, on photoexcitation, insert into a purine to give a purine nucleoside. These same cyclobutanones can also, upon photoexcitation, insert into ROH functions to give an intermediate in the preparation of a nucleoside or nucleoside analog. Accordingly, preparation of a purine nucleoside or a nucleoside analog is accomplished by a much shorter route and can be efficiently directed to produce novel purine nucleosides or a nucleoside analog. Furthermore, the process of the present invention can be efficiently directed to produce novel nucleosides or nucleoside analogs for testing as anti-viral/anti-cancer agents.

We have also found that a substantially optically pure cyclobutanone can insert into a purine or an alcohol to give a substantially optically pure (eg. >98% purity) nucleoside or an intermediate in the preparation of a nucleoside, respectively. Compounds of formulae 1, 2, and 3 have been found to show substantially the same optical purity as the cyclobutanones from which they are made. This finding would be applicable to other purine nucleosides, and nucleoside analogs (purine or pyrimidine) and intermediates in the preparation of these other purine nucleosides and nucleoside analogs. Accordingly, cyclobutanones of suitable optical purity are useful to prepare compounds to at least a standard of purity required by legislation governing production of relevant chiral medicinal agents.

Nucleoside intermediates (ie, intermediates in the preparation of both purine and pyrimidine nucleosides and analogs thereof), in their α- and β-anomeric forms, or enantiomers thereof, can be converted into nucleosides or nucleoside analogs, by standard chemical processes (Svansson, L. et al., ibid.).

SUMMARY OF THE INVENTION

The invention is directed to the preparation of optically active, preferably substantially optically pure, purine nucleosides, nucleoside analogs (purine or pyrimidine) and nucleoside intermediates.

In one aspect, the present invention is directed to a process for the preparation of an optically active purine nucleoside, nucleoside analog (purine or pyrimidine) or nucleoside intermediate of the formulae

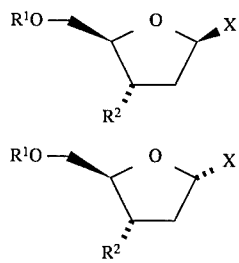

(or the enantiomeric forms thereof), wherein $R^1$ is an alcohol protecting group, $R^2$ is protected hydroxy, a removable group for E2 elimination or preferably hydrogen or alkoxymethyl (the alkyl group is an alcohol protecting group) and X is OR (R is a hydrocarbon, preferably a saturated hydrocarbon, more preferably a lower unbranched alkyl group having up to 4 carbons), a purine or pyrimidine analog wherein X—H incorporates an acidic N—H function (preferably a purine or pyrimidine analog not containing a carbonyl group) or more preferably a purine (preferably a purine not containing a carbonyl group), preferably a purin-9-yl (preferably a purin-9-yl not containing a carbonyl group), more preferably a purine substituent of the formula

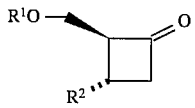

by exposing to UV light a solution (preferably degassed) comprising:

(a) an optically active, preferably substantially optically pure, cyclobutanone having the formula

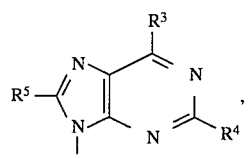

(or the enantiomeric form thereof, respectively) wherein $R^1$ and $R^2$ are as specified, respectively, above;

(b) a compound X—H, preferably in excess relative to compound 5 (>1.0:1.0 molar equivalents), wherein X is as specified above, and (c) where X is OR derived from a solid ROH or as otherwise specified above, a suitable aprotic solvent (capable of solubilizing compound 5 and X—H), preferably a dipolar aprotic solvent, more preferably a solvent selected from the group consisting of tetrahydrofuran, acetonitrile, dimethylformamide, dioxane and dimethylsulfoxide or mixtures thereof, more preferably selected from tetrahydrofuran or acetonitrile;

and preferably obtaining an anomeric mixture of compounds A and B having an optical purity substantially corresponding to the optical purity of the cyclobutanone (ie. removing the solvent).

The foregoing process may be carried out stepwise by:

1) preparing the solution comprising the cyclobutanone, the compound X—H and optionally the suitable aprotic solvent, as specified;

2) preferably, degassing the solution;

3) exposing the solution to UV light; and 4) preferably, obtaining an anomeric mixture of compounds A and B; and more preferably 5) purifying the mixture, preferably by chromatography or crystallization, to obtain at least one of compounds A or B. It is understood that the alcohol protecting group can be removed prior to or following purification of one or both of compounds 1 and 2.

Chiral cyclobutanones or nucleoside active compounds exhibiting a standard of purity required by legislation governing production of relevant chiral medicinal agents or greater are herein referred to as substantially optically pure. Preferably, the cyclobutanones are >98% optically pure and thereby result in the production of nucleoside active compounds of substantially corresponding optical purity (approx. 98% or more). Accuracy of the NMR analysis precludes the assessment of whether 100% purity is obtained. The term nucleoside analog (or purine or pyrimidine analog) as used herein refers to non-nucleoside compounds which mimic nucleosides and possibly interfere with nucleoside metabolic processes. The term nucleoside as used herein refers generally to a glycosylamine in which the amino component is a pyrimidine or a purine and in which the sugar component is a ribose derivative (compound 5, $R^1$=alkoxymethyl) and may refer herein, depending on the context, to protected or deprotected nucleosides.

In one preferred aspect, the present invention provides a process for the preparation of optically active purine nucleosides of formulae

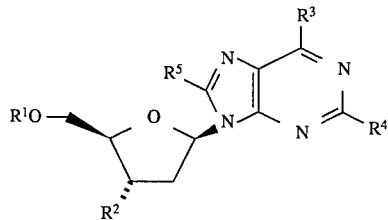

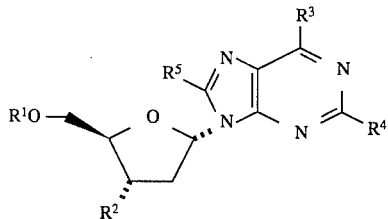

(or the enantiomeric forms thereof), wherein $R^1$ is an alcohol protecting group, $R^2$ is protected hydroxy, a removable group for E2 elimination or preferably hydrogen or alkoxymethyl (the alkoxy group is an alcohol protecting group), $R^3$ is hydrogen, $NH_2$, halogen or alkoxy (the alkoxy group having a branched or unbranched chain of preferably 1 to 18 carbons), preferably hydrogen or alkoxy (preferably methoxy or hexyloxy), $R^4$ is hydrogen, $NH_2$, halogen, alkoxy (the alkoxy group having a branched or unbranched chain of preferably 1 to 18 carbons), preferably hydrogen and $R^5$ is hydrogen, $NH_2$, halogen, alkoxy (the alkoxy group having a branched or unbranched chain of preferably 1 to 18 carbons), by exposing to ultraviolet light a solution (preferably degassed) comprising (a) an optically active, preferably substantially optically pure, cyclobutanone having the formula

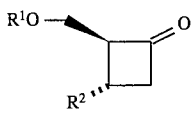    5

(or the enantiomeric form thereof, respectively) wherein $R^1$ and $R^2$ are as specified, respectively, above;
(b) a soluble compound of the formula

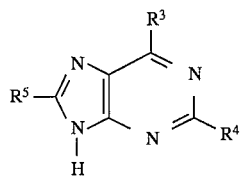    6 preferably in excess relative to compound 5 (>1.0:1.0 molar equivalents), wherein $R^3$, $R^4$ and $R^5$ are as specified respectively above; and
(c) a suitable aprotic solvent (capable of solubilizing compound 5 and 6), preferably a dipolar aprotic solvent, more preferably selected from the group consisting of tetrahydrofuran, acetonitrile, dimethylformamide, dioxane and dimethylsulfoxide and mixtures thereof, more preferably selected from tetrahydrofuran and acetonitrile;
obtaining an anomeric mixture of compounds 1 and 2 having an optical purity substantially corresponding to the optical purity of the cyclobutanone and preferably purifying the mixture, preferably by chromatography or crystallization, to obtain at least one of compounds 1 or 2.

The foregoing process may be carried out stepwise, prior to purification, by:

a) preparing the solution comprising the cyclobutanone, the compound of the formula 6 and the suitable aprotic solvent, as specified;
2) preferably, degassing the solution;
3) exposing the solution to UV light; and
4) obtaining the anomeric mixture of compounds 1 and 2.

In a further preferred aspect, the invention is directed to a process for the preparation of the optically active compounds of the formula

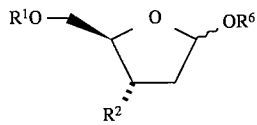    3

(or the enantiomeric forms thereof) wherein $R^1$ is an alcohol protecting group (preferably benzoyl) and $R^2$ is protected hydroxy, a removable group for E2 elimination such as selenophenoxy or thiophenoxy or preferably hydrogen or alkoxymethyl (the alkoxy group is an alcohol protecting group), $R^6$ is a hydrocarbon group, preferably a saturated hydrocarbon, more preferably a lower unbranched alkyl group having up to 4 carbons, which comprises the steps of:
1) exposing to ultraviolet light a preferably degassed solution comprising a) an optically active, preferably substantially optically pure, cyclobutanone of the formula

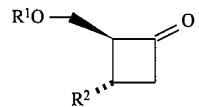    5

(or the enantiomeric form thereof, respectively) wherein $R^1$ and $R^2$ are as specified, respectively, above; and
b) a solvent selected from the group consisting of pure liquid alcohol and a mixture of an alcohol and a suitable aprotic solvent (capable of solubilizing compound 5 and the alcohol) preferably a dipolar aprotic solvent, more preferably selected from the group consisting of tetrahydrofuran, acetonitrile, dimethylformamide, dioxane and dimethylsulfoxide or mixtures thereof, more preferably selected from tetrahydrofuran or acetonitrile, more preferably tetrahydrofuran; and preferably
2) obtaining an anomeric mixture of compounds 3 having an optical purity substantially corresponding to the optical purity of the cyclobutanone; and preferably
3) purifying the mixture, preferably by chromatography or crystallization, to obtain at least one anomeric form of optically active compound 3. It is understood that the alcohol protecting group can be removed prior to or following purification of one or both anomeric forms of 3.

The foregoing process may be carried out stepwise, prior to purification, by:

1) preparing the solution comprising the cyclobutanone 5 and the solvent, as specified;
2) preferably, degassing the solution;
3) exposing the solution to UV light; and preferably
4) obtaining the anomeric mixture of compounds of the formula 3.

The process of the invention permits preparation of novel compounds A and B including novel intermediates 3 and novel nucleosides of formulae 1 and 2. The process of the invention preferably permits preparation of an intermediate of formulae 3 wherein $R^1$ is an alcohol protecting group, $R^2$ is benzoyloxymethyl or preferably hydrogen, and $R^6$ is a hydrocarbon group. The process of the invention preferably permits preparation of specific protected purine nucleosides of formulae 1 and 2 as follows:

1-N-(6-Methoxypurin-9-yl)-5-O-benzoyl-3-C-[(benzoyloxy)methyl]-2,3-dideoxy-α- and β-erythro-furanoside 1 and 2 ($R^1$=benzoyl, $R^2$=benzoyloxymethyl, $R^3$=OCH$_3$, $R^4$=$R^5$=H),

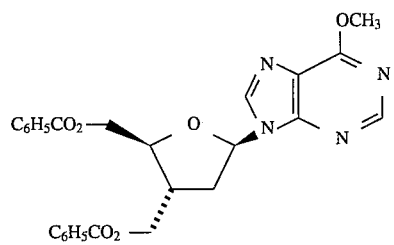

-continued

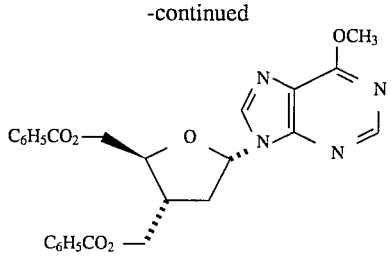

1-N-(6-n-Hexyloxypurin-9-yl)-5-O-benzoyl-3-C-[(benzoyloxy)methyl]-2,3-dideoxy-α- and β-erythro-furanoside 1 and 2 (R$^1$=benzoyl, R$^2$=benzoyloxymethyl, R$^3$=O(CH$_2$)$_5$CH$_3$, R$^4$=R$^5$=H),

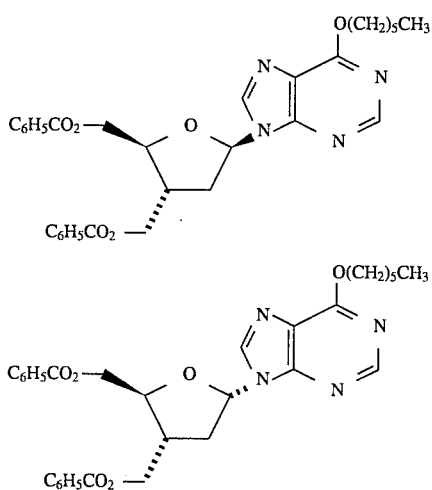

and to the deprotected forms of the above nucleosides as well as
1-N-(6-Methoxypurin-9-yl)-5-O-benzoyl-2,3-dideoxy-α- and β-erythrofuranoside 1 and 2 (R$^1$=benzoyl, R$^2$=H, R$^3$=OCH$_3$, R$^4$=R$^5$=H)

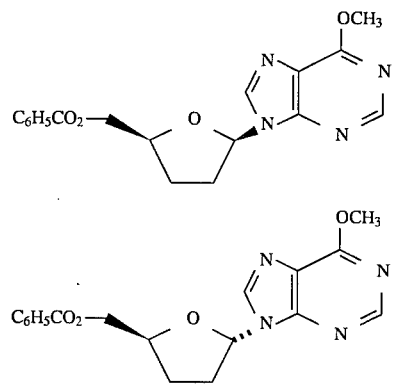

It is understood that the invention is also directed to the preparation of the enantiomeric forms of compounds A and B including compounds 1, 2, and 3 by the use of the enantiomers of the starting material of formula 5 and to the enantiomeric forms of the specific compounds described above.

DETAILED DESCRIPTION OF PREFERRED EMBODIMENTS

The invention is directed to the preparation of optically active, preferably substantially optically pure, purine nucleosides, nucleoside analogs (purine or pyrimidine) and nucleoside intermediates.

The process of the invention may be illustrated by the reaction scheme below:

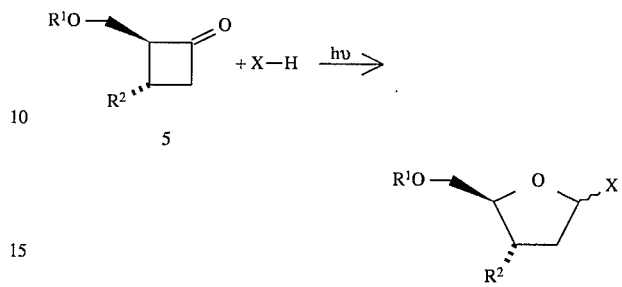

As indicated above, the process of the invention may be used to produce purine nucleosides other than compounds of the formula 1 and 2, and nucleoside analogs by using other purine bases or suitable purine and pyrimidine analogs as starting materials. Suitable purine and pyrimidine analogs are those incorporating an acidic N—H function. Preferably, R$^1$ is an alcohol protecting group, R$^2$ is protected hydroxy, a removable group for E2 elimination or preferably hydrogen or alkoxymethyl (the alkyl group is an alcohol protecting group) and X is OR (R is a hydrocarbon, preferably a saturated hydrocarbon, more preferably a lower unbranched alkyl group having up to 4 carbons), a purine or pyrimidine analog wherein X—H incorporates an acidic N—H function (preferably a purine or pyrimidine analog not containing a carbonyl group) or more preferably a purine (preferably a purine not containing a carbonyl group), preferably a purin-9-yl (preferably a purin-9-yl not containing a carbonyl group), more preferably a purine substituent of the formula

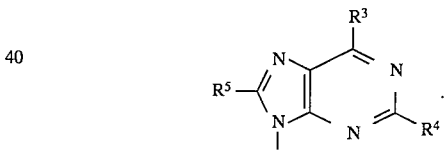

In preferred aspects, the process of the present invention is shown in the reaction schemes below:

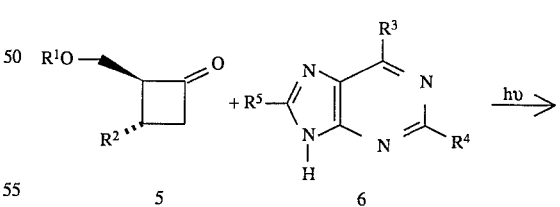

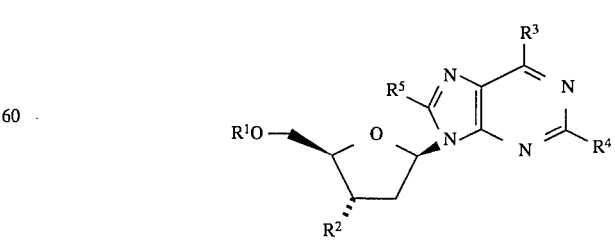

1

-continued

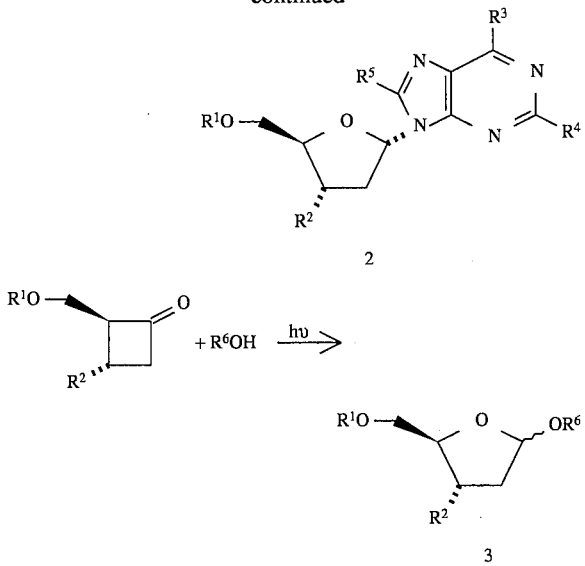

wherein $R^1$ is a protecting group such as aroyl, alkanoyl or a trialkylsilyl and $R^2$ is protected hydroxy or preferably hydrogen, alkoxymethyl (the alkoxy group is an alcohol protecting group) or a removable group for E2 elimination, $R^3$ is hydrogen, $NH_2$, halogen and alkoxy (the alkoxy group having a branched or unbranched chain of preferably 1 to 18 carbons), $R^4$ is hydrogen, $NH_2$, alkoxy (the alkoxy group having a branched or unbranched chain of preferably 1 to 18 carbons), $R^5$ is hydrogen, $NH_2$, alkoxy (the alkoxy group having a branched or unbranched chain of preferably 1 to 18 carbons) and $R^6$ is a hydrocarbon group, preferably lower alkyl groups. Compounds of the formulae 1, 2, and 3 wherein $R^2$=hydrogen or alkoxymethyl are indicated as preferred because the corresponding chiral cyclobutanones 5 are more readily available by reported published methods referred to below.

Further preferred features of the invention will now be described.

The process of the invention permits preparation of novel compounds A and B including novel intermediates 3 and novel nucleosides of formulae 1 and 2. The process of the invention preferably permits preparation of an intermediate of formulae 3 wherein $R^1$ is an alcohol protecting group, $R^2$ is alkoxy or preferably hydrogen, and $R^6$ is a hydrocarbon group, particularly $R^2$ is hydrogen. The process of the invention preferably permits preparation of specific protected purine nucleosides of formulae 1 and 2 wherein $R^1$ is an alcohol protecting group preferably benzoyl, benzyl, 2-tetrahydropyranyl and trimethylsilyl, $R^2$ is hydrogen, alkoxymethyl (the alkyl group is an alcohol protecting group selected from the list as specified for $R^1$), protected hydroxy group (the alkyl group is an alcohol protecting group selected from the list as specified for $R^1$) or a removable group for E2 elimination preferably, thiophenoxy, selenophenoxy or para-toluenesulfonoxy and $R^3$, $R^4$ and $R^5$ are hydrogen, amino, halogen (selected from the group consisting of fluorine, chlorine and bromine), alkoxy (unbranched chain of preferably 1 to 18 carbons and alkoxy groups derived from alcohols with saturated monocyclic, bicyclic, tricyclic and tetracyclic ring systems preferably up to 20 carbons).

Preferred $R^1$ groups are benzoyl and trialkylsily. More preferred $R^2$ groups are hydrogen and protected hydroxymethyl where the protecting group is either benzoyl or trialkylsilyl. The preferred $R^3$ and $R^4$ purine groups are for $R^3$=hydrogen, chlorine, methoxyl, n-hexyloxyl, $R^4$=hydrogen and $R^5$=hydrogen.

A substantially optically pure compound of formula 5 ($R^1$=benzoyl, $R^2$=benzoyloxymethyl) can be readily prepared by methods known in the art (see Ahmad, S., Tetrahedron Lett. (1991), vol. 32, p. 6997; Ahmad, S. Eur. Patent Appl. published under no. 0 458 643). A slight modification involving removal of the aluminum hydroxide salts by chromatography before crystallization of the initial cycloadduct derived from (−) dimenthyl fumarate and 1,1-dimethoxyethylene was used. The optically pure compound of formula 5 ($R^1$=benzoyl, $R^2$=hydrogen) can also be readily prepared by methods known in the art (see for example Narasaka, K. et al., Bull. Chem Soc. Jpn., (1991), vol. 64 p.1471). Chiral cyclobutanones may be prepared by general methods involving ketene-olefin cycloadditions where a chiral auxiliary is attached to either the ketene or olefin moiety (see for example Collington, E. W. et al., J. Chem. Soc. Perkin Trans. 1, (1990), p. 1839). Many purine derivatives of the formula 6 are commercially available (eg formula 6 $R^3$=$R^4$=$R^5$=H and formula 6 $R^3$=Cl, $R^4$=$R^5$=H are available from Aldrich Chemicals) or synthesized from commercially available purines by standard chemical transformations (see Shaw, G., in "Comprehensive Heterocyclic Chemistry" Katritzky, A. R. and Rees, C. W. (Ed), vol 5, p. 499, Pergamon Press (1984).

Purine nucleosides and nucleoside analogs of the formula A and B, particularly preferred and more preferred such compounds, may generally be prepared and purified according the standard techniques specified below, particularly the techniques and procedures referred to below for compounds of formulae 1 and 2. The compounds of formulae 1 and 2 may be prepared by irradiating preferably degassed solutions of compounds 5 and 6 in acetonitrile, dioxane, tetrahydrofuran, dimethylformamide or other aprotic solvent capable of solubilizing these compounds, preferably a dipolar aprotic solvent, preferably in pyrex tubes with a UV light source, for example, a Hanovia 450-W medium pressure mercury arc lamp contained in a water cooled quartz immersion well. The solvents are commercially available.

It is preferred to use an excess of compound 6 relative to compound 5 (greater than a 1.0:1.0 molar ratio) to avoid unwanted products since oxacarbene from compound 5 will undergo competitive transformation. Too great an excess of compound 6 will cause compound 6 to absorb light therefore possibly affecting yields. Solutions of 1 equivalent of 5 and 1.2 equivalents of 6 are suitable and are preferably prepared in either tetrahydrofuran or acetonitrile. A variety of suitable concentrations may be used. Optionally the concentration is approximately $10^{-4}$ to $10^{-3}$ molar. The solution is preferably degassed, optionally by purging with dry nitrogen. Degassing is preferred to preclude oxygen from reacting with the oxacarbene, thereby improving yields. For irradiation the solution is optionally contained in a pyrex tube, which is advantageous for filtering light below 300 nm. The pyrex tubes are placed in proximity to a UV assembly and irradiated for a duration depending on the power of the lamp, concentration of the solution and absolute amounts of materials etc. Optimum irradiation times may be arrived at by monitoring the disappearance of the starting materials. The solvent is preferably evaporated under reduced pressure. On a small scale this may be accomplished by rotary evaporation. Preferably crystallization techniques or chromatography may be used to purify the residue. The residue may be chromatographed over silica gel by preparative thin-layer chromatography or column chromatography using a combination of cosolvent systems including ethyl acetate, methylene chloride and methanol to give compounds 1 and 2.

Nucleoside intermediates of the formula A and B, particularly preferred and more preferred such compounds may generally be prepared and purified according to standard techniques, as specified below, particularly the techniques and procedures specified below for compounds of formulae 3. The compound of formula 3 may be prepared by irradiating compound 5 preferably in a degassed solution of preferably pure liquid alcohol, preferably an alkanol of 1 to 6 carbons, branched or unbranched, or a solution comprising of an alcohol and a suitable aprotic solvent capable of solubilizing compound 5 and the alcohol, preferably a dipolar aprotic solvent, more preferably, tetrahydrofuran. Preferable ratios of alcohol to aprotic solvent are 1:10 to 1:1 by volume (in the case of tetrahydrofuran, optionally 1:10 by volume). The preferred irradiation time will depend on the factors described above. After evaporation of the solvent, the residue may be chromatographed preferably on silica gel by thin-layer chromatography or column chromatography giving the desired compound of formula 3.

Alternatively, the compounds 1, 2 and 3 may be purified by crystallization using standard techniques known in the art.

The following examples representing more specific embodiments of the invention are illustrative but should not be understood as limiting the invention.

EXAMPLE 1

1N-(6-Chloropurin-9-yl)-5-O-benzoyl-3-C-[(benzoyloxy)methyl]-2,3-dideoxy-α- and β-erythro-furanoside 1 and 2 ($R^1$=benzoyl, $R^2$=benzoyloxymethyl, $R^3$=Cl, $R^4$=$R^5$=H 2(S),3(R)-Bisbenzoyloxymethylcyclobutanone 5 ($R^1$=benzoyl, $R^2$=benzoyloxymethyl) (135 mg) and 6-chloropurine 6 ($R^3$=Cl, $R^4$=$R^5$=H) (92 mg) were dissolved in 150 ml dry acetonitrile. The solution was purged with dry nitrogen and irradiated for 36 hours with a UV light source (450 W) using the photochemical assembly described above. The solvent was evaporated under reduced pressure using a rotoevaporator. The residue was chromatographed by preparative thin-layer chromatography on silica gel using a 96:4 methylene chloride to methanol mixture as eluting solvent. A pale yellow solid representing the title compound was obtained, m.p. 56°–58° C. Amonia reaction of the title compound according to the procedure of Svansson et al. (ibid.) gives 7-[2',3' dideoxy-3'-C-(hydroxymethyl)-α- and -β-D-erythro-pentofuranosyl]adenine which has the same properties as those reported by Svansson et al. for the same product. Separation of the α- and β-anomers permitted an x-ray crystal analysis of the β-anomer confirming its absolute configuration (100% optically pure).

EXAMPLE 2

1-N-(6-Methoxypurin-9-yl)-5-O-benzoyl-3-C-[(benzoyloxy)methyl]-2,3-dideoxy-α- and β-erythro-furanoside 1 and 2 ($R^1$=benzoyl, $R^2$=benzoyloxymethyl, $R^3$=$OCH_3$, $R^4$=$R^5$=H)

2(S),3(R)-Bisbenzoyloxymethylcyclobutanone 5 ($R^1$=benzoyl, $R^2$=benzoyloxymethyl) (136 mg) and 6-methoxypurine 6 ($R^3$=$OCH_3$, $R^4$=$R^5$=H) (180 mg) were dissolved in 150 ml dry acetonitrile. The solution was irradiated for 36 hours with a UV light source (450 W) using the photochemical assembly described above. The solvent was evaporated under reduced pressure using a rotoevaporater. The residue was chromatographed by preparative thin-layer chromatography on silica gel using a 96:43 methylene chloride to methanol mixture as eluting solvent. The title compound was obtained in 80.6 mg as a crystalline compound.

EXAMPLE 3

1-N-(6-n-Hexyloxypurin-9-yl)-5-O-benzoyl-3-C-[(benzoyloxy)methyl]-2,3-dideoxy-α- and β-erythro-furanoside 1 and 2 ($R^1$=benzoyl, $R^2$=benzoyloxymethyl, $R^3$=$O(CH_2)_5CH_3$, $R^4$=$R^5$=H 2(S),3(R)-Bisbenzoyloxymethylcyclobutanone 5 ($R^1$=benzoyl, $R^2$=benzoyloxymethyl) (68 mg) and 6-n-hexyloxypurine 6 ($R^3$=$O(CH_2)_5CH_3$, $R^4$=$R^5$=H) (132 mg) were dissolved in 150 ml dry tetrahydrofuran. The solution was irradiated for 36 hours with a UV light source (450 W) using the photochemical assembly described above. The solvent was evaporated under reduced pressure using a rotoevaporater. The residue was chromatographed by preparative thin-layer chromatography on silica gel using a 2.5:1 ethyl acetate:hexane mixture as the eluting solvent. The main fraction was further separated on preparative thin-layer chromatography on silica gel using a 95:5 by volume methylene chloride:ethyl acetate mixture as the eluting solvent giving the separated title compounds 1 and 2 in 13.4 and 13.6 mg respectively.

EXAMPLE 4

1-N-(6-Methoxypurin-9-yl)-5-O-benzoyl-2,3-dideoxy-α- and β-erythro-furanoside 1 and 2 ($R^1$=benzoyl, $R^2$=H, $R^3$=$OCH_3$, $R^4$=$R^5$=H)

A solution containing 204 mg of 2(S)-benzoyloxymethylcyclobutanone 5 ($R^1$=benzoyl, $R^2$=hydrogen) and 225 mg of 6-methoxypurine 6 ($R^3$=$OCH_3$, $R^4$=$R^5$=hydrogen) in 100 ml of dry acetonitrile was purged with argon. The solution was irradiated with a UV light source (450 W) for 38 hours using an assembly described above. The solvent was evaporated under reduced pressure using a rotoevaporator and the residue chromatographed by preparative thin-layer chromatography on silica gel covered plates with elution by 9.5:5 by volume of methylene chloride giving 244 mg of the title compound as a yellow oil. This had an optical rotation $[\alpha]_D^{20}$=+2.14° (c 1.05, $CH_2Cl_2$).

EXAMPLE 5

Methyl 5-O-Benzoyl-3-C-[(benzoyloxy)methyl]-2,3-dideoxy-α- and -β-D-erythro-pentofuranoside 3 ($R^1$=benzoyl, $R^2$=benzoyloxymethyl)

A solution containing 102 mg of 2(S),3(R)-bisbenzoyloxycyclobutanone 5 ($R^1$=benzoyl, $R^2$=H) and 6.5 ml of methanol in 65 ml of tetrahydrofuran was irradiated for 2 hours with a UV light source (450 W) using the photochemical assembly described above. The solvent was evaporated under reduced pressure using a rotoevaporator and the residue was chromatographed on a column of silica gel using a 8:1 hexane:ethyl acetate mixture as the eluting solvent giving 33 mg of the title compound as an anomeric mixture. This mixture was separated by preparative thin-layer chromatography to give 15 mg of the β-anomer and 15 mg of the α-anomer. The optical rotation of the β-anomer was $[\alpha]_D^{20}$=–46.40° (c, 1.0, $CHCl_3$). The optical rotaion of the α-anomer was $[\alpha]_D^{20}$=+39.8° (c, 1.0, $CHCl_3$). The NMR spectrum of either anomer in the presence of Eu(thc)$_3$ indicated greater than 98% optical purity.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process for the preparation of an optically active purine nucleoside, purine nucleoside analog, pyrimidine nucleoside analog or nucleoside intermediate, of formulae $$R^1O \overset{}{\underset{R^2}{\diagdown}} \overset{O}{\diagup} X \qquad A$$

$$R^1O \overset{}{\underset{R^2}{\diagdown}} \overset{O}{\diagup} X \qquad B$$

(or the enantiomeric forms thereof), wherein
   $R^1$ is an alcohol protecting group,
   $R^2$ is a member selected from the group consisting of a protected hydroxy, a removable group for E2 elimination, hydrogen and alkoxymethyl (the alkyl group of the hydroxymethyl is an alcohol protecting group), and
   X is OR, R is a hydrocarbon, a purine analog or a pyrimidine analog, wherein X—H incorporates an acidic N—H function
which process comprises the steps of:
   1) preparing a solution comprising:
      (a) an optically active, cyclobutanone having the formula $$R^1O \overset{}{\underset{R^2}{\diagdown}} \overset{}{\diagup} =O \qquad 5$$

(or the enantiomeric form thereof, wherein $R^1$ and $R^2$ are as specified, respectively, above;
      (b) a compound X—H, wherein X is OR a purine analogue or a pyrimidine analogue, or as a hydrocarbon and X—H incorporates an acidic N—H function, such that when X is OR the acidic function is O—H, and when X is a purine analog or a pyrimidine analog, the acidic function is N—H;
      (c) where X—H is a solid, a suitable aprotic solvent capable of solubilizing compound 5 and X—H
   2) exposing the solution to UV light; and,
   3) obtaining an anomeric mixture of compounds A and B, said process having a yield of more than 30%.

2. The process according to claim 1 wherein X is a purine substituent of the formula and X—H is in excess relative to compound 5 (>1.0:1.0 molar equivalents).

3. The process according to claim 1 wherein X=OR (R is a hydrocarbon).

4. The process according to claim 2 or 3 further comprising the step of purifying the mixture to obtain at least one of compounds A and B.

5. The process according to claim 4 further comprising the step of r6moving the alcohol protecting group(s).

6. The process according to claim 5 wherein the alcohol protecting group(s) is removed prior to the purification of one or both of compounds A and B.

7. The process according to claim 1 wherein the yield is greater than 42.5%.

8. A process for the preparation of optically active purine nucleosides of formulae (or the enantiomeric forms thereof), wherein
   $R^1$ is an alcohol protecting group,
   $R^2$ is a protected hydroxy, a removable group for E2 elimination, hydrogen or alkoxymethyl (the alkoxy group is an alcohol protecting group),
   $R^3$ $R^4$ and $R^5$ are each individually selected from the group consisting of hydrogen, $NH_2$, halogen and alkoxy (the alkoxy group having a branched or unbranched chain of 1 to 18 carbons),
which comprises the steps of:
   1) preparing a solution comprising:
      a) an optically active, cyclobutanone having the formula $$R^1O \overset{}{\underset{R^2}{\diagdown}} \overset{}{\diagup} =O \qquad 5$$

(or the enantiomeric form thereof, respectively) wherein $R^1$ and $R^2$ are as specified, respectively, above;
      b) a compound of the formula and
      c) a suitable aprotic solvent (capable of solubilizing compounds 5 and 6),
   2) exposing the solution to UV light; and,
   3) obtaining an anomeric mixture of compounds 1 and 2, said process having a yield of more than 30%.

9. The process according to claim 8 wherein the ratio of compound 6 to compound 5 is greater than 1.0:1.0 molar equivalents.

10. The process according to claim 9 further comprising the step of purifying at least one of compounds 1 and 2.

11. The process according to claim 10 further comprising the step of removing the alcohol protecting group.

12. The process according to claim 11 wherein the alcohol protecting group is removed prior to the purification of one or both of compounds 1 and 2.

13. The process according to claim 8 wherein the yield is greater than 42.5%.

14. A process for the preparation of the optically active compounds of the formula

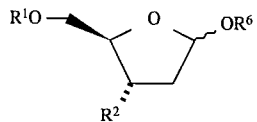  3

(or the enantiomeric forms thereof) wherein
$R^1$ is an alcohol protecting group, and
$R^2$ is a protected hydroxy, a removable group for E2 elimination, hydrogen or alkoxymethyl (the alkoxy group is an alcohol protecting group),
$R^6$ is a hydrocarbon group,
which compromises
1) preparing a solution comprising:
   a) an optically active, cyclobutanone of the formula

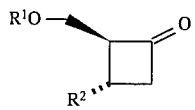  5

(or the enantiomeric form thereof, respectively) wherein $R^1$ and $R^2$ are as specified, respectively, above; and $R^6OH$ 2) exposing the solution to UV light; and 3) obtaining an anomeric mixture of compounds 3, said process having a yield of more than 30%.

15. The process according to claim 14 further comprising the step of purifying at least one of the anomeric forms of compound 3.

16. The process according to claim 15 further comprising the step of removing the alcohol protecting group.

17. The process according to claim 16 wherein the alcohol protecting group(s) is removed prior to the purification of one or both of the anomeric forms of compound 3.

18. The process according to claim 14 wherein the alcohol protecting groups are removed prior to removing the solvent.

19. The process according to claim 14 wherein $R^1$ is an alcohol protecting group and $R^2$ is hydrogen or the enantiomeric form thereof.

20. The process according to claim 14 wherein the yield is greater than 42.5%.

21. The process according to claim 14 wherein said said solution further comprises a suitable aprotic solvent capable of solubilizing compound 5 and the alcohol.

* * * * *